United States Patent
Tsai et al.

(10) Patent No.: US 6,197,237 B1
(45) Date of Patent: *Mar. 6, 2001

(54) METHOD OF MAKING A MULTICOMPONENT FIBER AND NONWOVEN WEB CONTAINING THE SAME

(75) Inventors: Fu-Jya Daniel Tsai; Brian Thomas Etzel, both of Appleton, WI (US)

(73) Assignee: Kimberly Clark Corporation, Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,864

(22) Filed: Jun. 8, 1999

Related U.S. Application Data

(63) Continuation of application No. 08/995,982, filed on Dec. 22, 1997, now Pat. No. 5,952,088.

(51) Int. Cl.⁷ .................. D01F 8/06; D01F 8/14
(52) U.S. Cl. .............. 264/172.13; 264/172.11; 264/172.14; 264/172.15; 428/221; 428/297.4; 428/299.7; 428/300.7; 428/480; 525/166; 525/177; 525/186; 525/190; 524/378; 524/513

(58) Field of Search .............. 264/172.11, 172.13, 264/172.14, 172.15; 524/378, 513; 525/166, 177, 186, 190; 428/221, 297.4, 299.7, 300.7, 480

(56) References Cited

FOREIGN PATENT DOCUMENTS 92 04410 * 3/1992 (WO) .

* cited by examiner

*Primary Examiner*—Patricia A. Short
(74) *Attorney, Agent, or Firm*—Kilpatrick Stockton, LLP

(57) ABSTRACT

Disclosed is a thermoplastic composition comprising an unreacted mixture of an aliphatic polyester polymer as a continuous phase, polyolefin microfibers as a discontinuous phase encased within the aliphatic polyester polymer continuous phase, and a compatibilizer for the aliphatic polyester polymer and the polyolefin microfibers. The multicomponent fiber exhibits substantial biodegradable properties and good wettability yet is easily processed. The thermoplastic composition is useful in making nonwoven structures that may be used in a disposable absorbent product intended for the absorption of fluids such as body fluids.

20 Claims, No Drawings

METHOD OF MAKING A MULTICOMPONENT FIBER AND NONWOVEN WEB CONTAINING THE SAME

This application is a continuation of U.S. patent application Ser. No. 08/995,982 filed on Dec. 22, 1997, now U.S. Pat. No. 5,952,088.

FIELD OF THE INVENTION

The present invention relates to a multicomponent fiber. The multicomponent fiber comprises an unreacted mixture of an aliphatic polyester polymer as a continuous phase, polyolefin microfibers as a discontinuous phase encased within the aliphatic polyester polymer continuous phase, and a compatibilizer for the aliphatic polyester polymer and the polyolefin microfibers. The multicomponent fiber exhibits substantial biodegradable properties yet is easily processed. The multicomponent fiber is useful in making nonwoven structures that may be used in a disposable absorbent product intended for the absorption of fluids such as body fluids.

BACKGROUND OF THE INVENTION

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These products usually include some type of fastening system for fitting the product onto the wearer.

Disposable absorbent products are typically subjected to one or more liquid insults, such as of water, urine, menses, or blood, during use. As such, the outer cover backsheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable baby diapers and other disposable absorbent products have been generally accepted by the public, these products still have need of improvement in specific areas. For example, many disposable absorbent products can be difficult to dispose of. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way. If the outer cover materials are made very thin in order to reduce the overall bulk of the disposable absorbent product so as to reduce the likelihood of blockage of a toilet or a sewage pipe, then the outer cover material typically will not exhibit sufficient strength to prevent tearing or ripping as the outer cover material is subjected to the stresses of normal use by a wearer.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that can be disposed of by means other than by incorporation into solid waste disposal facilities such as landfills.

As such, there is a need for new materials that may be used in disposable absorbent products that generally retain their integrity and strength during use, but after such use, the materials may be more efficiently disposed of. For example, the disposable absorbent product may be easily and efficiently disposed of by composting. Alternatively, the disposable absorbent product may be easily and efficiently disposed of to a liquid sewage system wherein the disposable absorbent product is capable of being degraded.

Although degradable monocomponent fibers are known, problems have been encountered with their use. In particular, known degradable fibers typically do not have good thermal dimensional stability such that the fibers usually undergo severe heat-shrinkage due to the polymer chain relaxation during downstream heat treatment processes such as thermal bonding or lamination.

In contrast, polyolefin materials, such as polypropylene, typically exhibit good thermal dimensional stability but also have problems associated with their use. In particular, polyolefin fibers typically are hydrophobic and, and such, exhibit poor wettability, thus limiting their use in disposable absorbent products intended for the absorption of fluids such as body fluids. Although surfactants can be used to improve the wettability of polyolefin fibers, the use of such surfactants introduces additional problems such as added cost, fugitivity or permanence, and toxicity. Furthermore, polyolefin fibers are generally not biodegradable or compostable.

It would therefore be desirable to prepare a fiber that exhibits the thermal dimensional stability of polyolefin materials yet is substantially biodegradable and is wettable without the use of surfactants. A simple solution to this desire would be to simply mix a polyolefin material with a degradable material so as to gain the benefits of using both materials. However, the components of a multicomponent fiber generally need to be chemically compatible, so that the components effectively adhere to each other, and have similar rheological characteristics, so that the multicomponent fiber exhibits minimum strength and other mechanical and processing properties. It has therefore proven to be a challenge to those skilled in the art to combine components that meet these basic processing needs as well as meeting the desire that the entire multicomponent fiber be effectively substantially degradable and hydrophilic.

It is therefore an object of the present invention to provide a multicomponent fiber which is substantially degradable in the environment.

It is also an object of the present invention to provide a substantially degradable multicomponent fiber which has good thermal dimensional stability and is hydrophilic without the substantial use of surfactants.

It is also an object of the present invention to provide a substantially degradable multicomponent fiber which is easily and efficiently prepared and which is suitable for use in preparing nonwoven structures.

SUMMARY OF THE INVENTION

The present invention concerns a thermoplastic composition that is substantially biodegradable and yet which is easily prepared and readily processable into desired final structures, such as fibers or nonwoven structures.

One aspect of the present invention concerns a thermoplastic composition that comprises a mixture of a first component, a second component, and a third component.

One embodiment of such a thermoplastic composition comprises an unreacted mixture of an aliphatic polyester polymer as a substantially continuous phase, polyolefin microfibers as a substantially discontinuous phase encased within the aliphatic polyester polymer substantially continuous phase, and a compatibilizer for the aliphatic polyester polymer and the polyolefin microfibers.

In another aspect, the present invention concerns a multicomponent fiber that is substantially degradable and yet which is easily prepared and readily processable into desired final structures, such as fibers or nonwoven structures.

One aspect of the present invention concerns a multicomponent fiber that comprises an unreacted mixture of an aliphatic polyester polymer as a substantially continuous phase, polyolefin microfibers as a substantially discontinuous phase encased within the aliphatic polyester polymer substantially continuous phase, and a compatibilizer for the aliphatic polyester polymer and the polyolefin microfibers.

In another aspect, the present invention concerns a nonwoven structure comprising the multicomponent fiber disclosed herein.

One embodiment of such a nonwoven structure is a backsheet useful in a disposable absorbent product.

In another aspect, the present invention concerns a disposable absorbent product comprising the multicomponent fiber disclosed herein.

In another aspect, the present invention concerns a process for preparing the multicomponent fiber disclosed herein.

DETAILED DESCRIPTION OF THE PREFERRED EMBODIMENTS

The present invention is directed to a thermoplastic composition which includes a first component, a second component, and a third component. As used herein, the term "thermoplastic" is meant to refer to a material that softens when exposed to heat and substantially returns to its original condition when cooled to room temperature.

It has been discovered that, by using an unreacted mixture of an aliphatic polyester polymer as a substantially continuous phase, polyolefin microfibers as a substantially discontinuous phase encased within the aliphatic polyester polymer substantially continuous phase, and a compatibilizer for the aliphatic polyester polymer and the polyolefin microfibers, a thermoplastic composition may be prepared wherein such thermoplastic composition is substantially degradable yet which thermoplastic composition is easily processable into fibers and nonwoven structures that exhibit effective fibrous mechanical properties and liquid handling properties.

The first component in the thermoplastic composition is an aliphatic polyester polymer. Suitable aliphatic polyester polymers include, but are not limited to, poly(lactic acid), polybutylene succinate, polybutylene succinate-co-adipate, polyhydroxybutyrate-co-valerate, polycaprolactone, sulfonated polyethylene terephthalate, mixtures of such polymers, or copolymers of such polymers.

In one embodiment of the present invention, it is desired that the aliphatic polyester polymer used is poly(lactic acid). Poly(lactic acid) polymer is generally prepared by the polymerization of lactic acid. However, it will be recognized by one skilled in the art that a chemically equivalent material may also be prepared by the polymerization of lactide. As such, as used herein, the term "poly(lactic acid) polymer" is intended to represent the polymer that is prepared by either the polymerization of lactic acid or lactide.

Lactic acid and lactide are known to be asymmetrical molecules, having two optical isomers referred to, respectively, as the levorotatory (hereinafter referred to as "L") enantiomer and the dextrorotatory (hereinafter referred to as "D") enantiomer. As a result, by polymerizing a particular enantiomer or by using a mixture of the two enantiomers, it is possible to prepare different polymers that are chemically similar yet which have different properties. In particular, it has been found that by modifying the stereochemistry of a poly(lactic acid) polymer, it is possible to control, for example, the melting temperature, melt rheology, and crystallinity of the polymer. By being able to control such properties, it is possible to prepare a multicomponent fiber exhibiting desired melt strength, mechanical properties, softness, and processability properties so as to be able to make attenuated, heat set, and crimped fibers.

It is generally desired that the aliphatic polyester polymer be present in the thermoplastic composition in an amount effective to result in the thermoplastic composition exhibiting desired properties. The aliphatic polyester polymer will be present in the thermoplastic composition in a weight amount that is less than 100 weight percent, beneficially between about 45 weight percent to about 90 weight percent, suitably between about 50 weight percent to about 88 weight percent, and more suitably between about 55 weight percent to about 70 weight percent, wherein all weight percents are based on the total weight amount of the aliphatic polyester polymer, the polyolefin microfiber, and the compatibilizer present in the thermoplastic composition. The compositional ratio of the three components in the thermoplastic composition is generally important to maintaining the substantial biodegradability of the thermoplastic composition because the aliphatic polyester polymer generally needs to be in a substantially continuous phase in order to maintain access to the biodegradable portion of the thermoplastic composition. An approximation of the limits of component ratios can be determined based on the densities of the components. The density of a component is converted to a volume (assume 100 g of each component), the volumes of the components are added together for a total thermoplastic composition volume and the components' weight averages calculated to establish the approximate minimum ratio of each component needed to produce a thermoplastic composition with a volumetric majority of the aliphatic polyester polymer in the blend.

It is generally desired that the aliphatic polyester polymer exhibit a weight average molecular weight that is effective for the thermoplastic composition to exhibit desirable melt strength, fiber mechanical strength, and fiber spinning properties. In general, if the weight average molecular weight of an aliphatic polyester polymer is too high, this represents that the polymer chains are heavily entangled which may result in a thermoplastic composition comprising that aliphatic polyester polymer being difficult to process. Conversely, if the weight average molecular weight of an aliphatic polyester polymer is too low, this represents that the polymer chains are not entangled enough which may result in a thermoplastic composition comprising that aliphatic polyester polymer exhibiting a relatively weak melt strength, making high speed processing very difficult. Thus, aliphatic polyester polymers suitable for use in the present invention exhibit weight average molecular weights that are beneficially between about 10,000 to about 2,000,000, more beneficially between about 50,000 to about 400,000, and suitably between about 100,000 to about 300,000. The weight average molecular weight for polymers or polymer blends can be determined using a method as described in the Test Methods section herein.

It is also desired that the aliphatic polyester polymer exhibit a polydispersity index value that is effective for the thermoplastic composition to exhibit desirable melt strength, fiber mechanical strength, and fiber spinning properties. As used herein, "polydispersity index" is meant to represent the value obtained by dividing the weight average molecular weight of a polymer by the number average molecular weight of the polymer. In general, if the polydispersity index value of an aliphatic polyester polymer is too high, a thermoplastic composition comprising that aliphatic polyester polymer may be difficult to process due to inconsistent processing properties caused by polymer segments comprising low molecular weight polymers that have lower melt strength properties during spinning. Thus, it is desired that the aliphatic polyester polymer exhibits a polydispersity index value that is beneficially between about 1 to about 15, more beneficially between about 1 to about 4, and suitably between about 1 to about 3. The number average molecular weight for polymers or polymer blends can be determined using a method as described in the Test Methods section herein.

In the present invention, it is desired that the aliphatic polyester polymer be biodegradable. As a result, the thermoplastic composition comprising the aliphatic polyester polymer, either in the form of a fiber or in the form of a nonwoven structure, will be substantially degradable when disposed of to the environment and exposed to air and/or water. As used herein, "biodegradable" is meant to represent that a material degrades from the action of naturally occurring microorganisms such as bacteria, fungi, and algae.

In the present invention, it is also desired that the aliphatic polyester polymer be compostable. As a result, the thermoplastic composition comprising the aliphatic polyester polymer, either in the form of a fiber or in the form of a nonwoven structure, will be substantially compostable when disposed of to the environment and exposed to air and/or water. As used herein, "compostable" is meant to represent that a material is capable of undergoing biological decomposition in a compost site such that the material is not visually distinguishable and breaks down into carbon dioxide, water, inorganic compounds, and biomass, at a rate consistent with known compostable materials.

The second component in the thermoplastic composition is polyolefin microfibers. Polyolefins are known to those skilled in the art. Any polyolefin capable of being fabricated into an article, such as a microfiber, is believed suitable for use in the present invention. Exemplary of polyolefins suitable for use in the present invention are the homopolymers and copolymers comprising repeating units formed from one or more aliphatic hydrocarbons, including ethylene, propylene, butene, pentene, hexene, heptene, octene, 1,3-butadiene, and 2-methyl-1,3-butadiene. The polyolefins may be high or low density and may be generally linear or branched chain polymers. Methods of forming polyolefins are known to those skilled in the art.

Polyolefins, such as those described above, are generally hydrophobic in nature. As used herein, the term "hydrophobic" refers to a material having a contact angle of water in air of at least 90 degrees. In contrast, as used herein, the term "hydrophilic" refers to a material having a contact angle of water in air of less than 90 degrees. For the purposes of this application, contact angle measurements may be determined as set forth in Robert J. Good and Robert J. Stromberg, Ed., in "Surface and Colloid Science—Experimental Methods", Vol. II, (Plenum Press, 1979), pages 63–70.

It is generally desired that both the aliphatic polyester polymer and the polyolefin be melt processable. It is therefore desired that the aliphatic polyester polymer and the polyolefin exhibit a melt flow rate that is beneficially between about 1 gram per 10 minutes to about 200 grams per 10 minutes, suitably between about 10 grams per 10 minutes to about 100 grams per 10 minutes, and more suitably between about 20 grams per 10 minutes to about 40 grams per 10 minutes. The melt flow rate of a material may be determined according to ASTM Test Method D1238-E incorporated in its entirety herein by reference.

In the present invention, the polyolefin is used in the form of a microfiber. As used herein, the term "microfiber" is meant to refer to a fibrous material having a diameter that is less than about 50 micrometers, beneficially less than about 25 micrometers more beneficially less than about 10 micrometers, suitably less than about 5 micrometers, and most suitably less than about 1 micrometer.

In one embodiment of the present invention, the polyolefin microfiber comprises a percentage of the cross sectional area of a multicomponent fiber prepared from the thermoplastic composition of the present invention that is effective for the multicomponent fiber to exhibit desirable melt strength, fiber mechanical strength, and fiber spinning properties. In general, if the polyolefin microfiber comprises a percentage of the cross sectional area of a multicomponent fiber that is too high, this generally results in a multicomponent fiber that will not be substantially biodegradable or that will be difficult to process. Conversely, if the polyolefin microfiber comprises a percentage of the cross sectional area of a multicomponent fiber that is too low, this generally results in a multicomponent fiber that will not exhibit effective structural properties or that may be difficult to process. Thus, the polyolefin microfiber desirably comprises a percentage of the cross sectional area of a multicomponent fiber that is beneficially less than about 20 percent of the cross sectional area of the multicomponent fiber, more beneficially less than about 15 percent of the cross sectional area of the multicomponent fiber, and suitably less than about 10 percent of the cross sectional area of the multicomponent fiber.

As used herein, the term "fiber" or "fibrous" is meant to refer to a material wherein the length to diameter ratio of such material is greater than about 10. Conversely, a "nonfiber" or "nonfibrous" material is meant to refer to a material wherein the length to diameter ratio of such material is about 10 or less.

The polyolefin is generally desired to be in the form of a microfiber so as to allow the polyolefin to effectively function as a structural support within the thermoplastic composition so as to prevent a substantial thermal dimensional-shrinkage of the thermoplastic composition during processing while generally maintaining a desired degree of substantial biodegradability of the thermoplastic composition.

It is generally desired that the polyolefin microfibers be present in the thermoplastic composition in an amount effective to result in the thermoplastic composition exhibiting desired properties. The polyolefin microfibers will be present in the thermoplastic composition in a weight amount that is beneficially between greater than 0 weight percent to about 45 weight percent, suitably between about 5 weight percent to about 40 weight percent, and more suitably between about 10 weight percent to about 30 weight percent, wherein all weight percents are based on the total weight amount of the aliphatic polyester polymer, the polyolefin microfiber, and the compatibilizer present in the thermoplastic composition. It is generally important for the polyolefin to be a substantially discontinuous phase of the thermoplastic composition so that the polyolefin microfibers can provide structural support to the thermoplastic composition or materials formed from the thermoplastic composition, such as fibers or nonwovens, without negatively affecting the biodegradability of the aliphatic polyester or of the substantial biodegradability of the thermoplastic composition or materials formed from the thermoplastic composition.

Either separately or when mixed together, the aliphatic polyester polymer and the polyolefin microfiber are generally hydrophobic. However, it is generally desired that the thermoplastic composition of the present invention, and fibers prepared from the thermoplastic composition, generally be hydrophilic so that such fibers are useful in disposable absorbent products which are insulted with aqueous liquids such as water, urine, menses, or blood. Thus, it has been found desirable to use another component as a surfactant in the thermoplastic composition of the present invention in order to achieve the desired hydrophilic properties.

Furthermore, it has been found desirable to improve the processability of the aliphatic polyester polymer and the polyolefin microfibers, since such polymers are not chemically identical and are, therefore, somewhat incompatible with each other which tends to negatively affect the processing of a mixture of such polymers. For example, the aliphatic polyester polymer and the polyolefin microfibers are sometimes difficult to effectively mix and prepare as an essentially homogeneous mixture on their own. Generally, then, it has been found desirable to use a compatibilizer to aid in the effective preparation and processing of the aliphatic polyester polymer and the polyolefin microfibers into a single thermoplastic composition.

Therefore, the third component in the thermoplastic composition is a compatibilizer for the aliphatic polyester polymer and the polyolefin microfibers. Compatibilizers suitable for use in the present invention will generally comprise a hydrophilic section which will generally be compatible to the aliphatic polyester polymer and a hydrophobic section which will generally be compatible to the polyolefin microfibers. These hydrophilic and hydrophobic sections will generally exist in separate blocks so that the overall compatibilizer structure may be di-block or random block. It is generally desired that the compatibilizer initially functions as a plasticizer in order to improve the preparation and processing of the thermoplastic composition. It is then generally desired that the compatibilizer serves as a surfactant in a material processed from the thermoplastic composition, such as a fiber or nonwoven structure, by modifying the contact angle of water in air of the processed material. The hydrophobic portion of the compatibilizer may be, but is not limited to, a polyolefin such as polyethylene or polypropylene. The hydrophilic portion of the compatibilizer may contain ethylene oxide, ethoxylates, glycols, alcohols or any combinations thereof. Examples of suitable compatibilizers include UNITHOX®480 and UNITHOX®750 ethoxylated alcohols, or UNICID® Acid Amide Ethoxylates, all available from Petrolite Corporation of Tulsa, Okla.

It is generally desired that the compatibilizer exhibit a weight average molecular weight that is effective for the thermoplastic composition to exhibit desirable melt strength, fiber mechanical strength, and fiber spinning properties. In general, if the weight average molecular weight of a compatibilizer is too high, the compatibilizer will not blend well with the other components in the thermoplastic composition because the compatibilizer's viscosity will be so high that it lacks the mobility needed to blend. Conversely, if the weight average molecular weight of the compatibilizer is too low, this represents that the compatibilizer will generally not blend well with the other components and have such a low viscosity that it causes processing problems. Thus, compatibilizers suitable for use in the present invention exhibit weight average molecular weights that are beneficially between about 1,000 to about 100,000, suitably between about 1,000 to about 50,000, and more suitably between about 1,000 to about 10,000. The weight average molecular weight for a compatibilizer material can be determined using methods known to those skilled in the art.

It is generally desired that the compatibilizer exhibit an effective hydrophilic-lipophilic balance ratio (HLB ratio). The HLB ratio of a material describes the relative ratio of the hydrophilicity of the material. The HLB ratio is calculated as the weight average molecular weight of the hydrophilic portion divided by the total weight average molecular weight of the material, which value is then multiplied by 20. If the HLB ratio value is too low, the material will generally not provide the desired improvement in hydrophilicity. Conversely, if the HLB ratio value is too high, the material will generally not blend into the thermoplastic composition because of chemical incompatibility and differences in viscosities with the other components. Thus, compatibilizers useful in the present invention exhibit HLB ratio values that are beneficially between about 10 to about 40, suitably between about 10 to about 20, and more suitably between about 12 to about 18.

It is generally desired that the compatibilizer be present in the thermoplastic composition in an amount effective to result in the thermoplastic composition exhibiting desired properties. In general, a minimal amount of the compatibilizer will be needed to achieve an effective blending and processing with the other components in the thermoplastic composition. In general, too much of the compatibilizer will lead to processing problems of the thermoplastic composition. The compatibilizer will be present in the thermoplastic composition in a weight amount that is beneficially between about 7 weight percent to about 25 weight percent, more beneficially between about 10 weight percent to about 25 weight percent, suitably between about 12 weight percent to about 20 weight percent, and more suitably between about 13 weight percent to about 18 weight percent, wherein all weight percents are based on the total weight amount of the aliphatic polyester polymer, the polyolefin microfiber, and the compatibilizer present in the thermoplastic composition.

While the principal components of the thermoplastic composition of the present invention have been described in the foregoing, such thermoplastic composition is not limited thereto and can include other components not adversely effecting the desired properties of the thermoplastic composition. Exemplary materials which could be used as additional components would include, without limitation, pigments, antioxidants, stabilizers, surfactants, waxes, flow promoters, solid solvents, plasticizers, nucleating agents, particulates, and materials added to enhance processability of the thermoplastic composition. If such additional components are included in a thermoplastic composition, it is generally desired that such additional components be used in an amount that is beneficially less than about 5 weight percent, more beneficially less than about 3 weight percent, and suitably less than about 1 weight percent, wherein all weight percents are based on the total weight amount of the aliphatic polyester polymer, the polyolefin microfiber, and the compatibilizer present in the thermoplastic composition.

The thermoplastic composition of the present invention is generally simply a mixture of the aliphatic polyester polymer, the polyolefin microfibers, the compatibilizer, and, optionally, any additional components. In order to achieve the desired properties for the thermoplastic composition of the present invention, it is desirable that the aliphatic polyester polymer, the polyolefin microfibers, and the compatibilizer remain substantially unreacted with each other. As such, each of the aliphatic polyester polymer, the polyolefin microfibers, and the compatibilizer remain distinct components of the thermoplastic composition. Furthermore, it is desired that the aliphatic polyester polymer form a substantially continuous phase and that the polyolefin microfibers form a substantially discontinuous phase, wherein the aliphatic polyester polymer continuous phase substantially encases the polyolefin microfibers within its structure. As used herein, the term "encase", and related terms, are intended to mean that the aliphatic polyester polymer continuous phase substantially encloses or surrounds the polyolefin microfibers.

In one embodiment of the present invention, after dry mixing together the aliphatic polyester polymer, the polyolefin microfibers, and the compatibilizer to form a thermoplastic composition dry mixture, such thermoplastic composition dry mixture is beneficially agitated, stirred, or otherwise blended to effectively uniformly mix the aliphatic polyester polymer, the polyolefin microfibers, and the compatibilizer such that an essentially homogeneous dry mixture is formed. The dry mixture may then be melt blended in, for example, an extruder, to effectively uniformly mix the aliphatic polyester polymer, the polyolefin microfibers, and the compatibilizer such that an essentially homogeneous melted mixture is formed. The essentially homogeneous melted mixture may then be cooled and pelletized. Alternatively, the essentially homogeneous melted mixture may be sent directly to a spin pack or other equipment for forming fibers or a nonwoven structure.

Alternative methods of mixing together the components of the present invention include first mixing together the aliphatic polyester polymer and the polyolefin microfibers and then adding the compatibilizer to such a mixture in, for example, an extruder being used to mix the components together. In addition, it is also possible to initially melt mix all of the components together at the same time. Other methods of mixing together the components of the present invention are also possible and will be easily recognized by one skilled in the art.

The present invention is also directed to a multicomponent fiber which is prepared from the thermoplastic composition of the present invention. For purposes of illustration only, the present invention will generally be described in terms of a multicomponent fiber comprising only three components. However, it should be understood that the scope of the present invention is meant to include fibers with three or more components. In one embodiment, the thermoplastic composition of the present invention may be used to form the sheath of a multicomponent fiber while a polyolefin, such as polypropylene or polyethylene, is used to form the core. Suitable structural geometries for multicomponent fibers include pie shape or side-by-side configurations.

With the aliphatic polyester polymer forming a substantially continuous phase, the aliphatic polyester polymer will generally provide an exposed surface on at least a portion of the multicomponent fiber which will generally permit thermal bonding of the multicomponent fiber to other fibers which may be the same or different from the multicomponent fiber of the present invention. As a result, the multicomponent fiber can then be used to form thermally bonded fibrous nonwoven structures such as a nonwoven web. The polyolefin microfibers in the multicomponent fiber generally provide strength or rigidity to the multicomponent fiber and, thus, to any nonwoven structure comprising the multicomponent fiber. In order to provide such strength or rigidity to the multicomponent fiber, it is generally desired that the polyolefin microfibers be substantially continuous along the length of the multicomponent fiber.

Typical conditions for thermally processing the various components include using a shear rate that is beneficially between about 100 seconds$^{-1}$ to about 10000 seconds$^{-1}$, more beneficially between about 500 seconds$^{-1}$ to about 5000 seconds$^{-1}$, suitably between about 1000 seconds$^{-1}$ to about 2000 seconds$^{-1}$, and most suitably at about 1000 seconds$^{-1}$. Typical conditions for thermally processing the components also include using a temperature that is beneficially between about 100° C. to about 500° C., more beneficially between about 150° C. to about 300° C., and suitably between about 175° C. to about 250° C.

Methods for making multicomponent fibers are well known and need not be described here in detail. The melt spinning of polymers includes the production of continuous filament, such as spinbonded or meltblown, and non-continuous filament, such as staple and short-cut fibers, structures. To form a spinbonded or meltblown fiber, generally, a thermoplastic composition is extruded and fed to a distribution system where the thermoplastic composition is introduced into a spinneret plate. The spun fiber is then cooled, solidified, and drawn by an aerodynamic system, to be formed into a conventional nonwoven. Meanwhile, to produce short-cut or staple fiber, rather than being directly formed into a nonwoven structure, the spun fiber is cooled, solidified, and drawn, generally by a mechanical rolls system, to an intermediate filament diameter and collected. Subsequently, the fiber may be "cold drawn" at a temperature below its softening temperature, to the desired finished fiber diameter and crimped or texturized and cut into a desirable fiber length.

The process of cooling an extruded thermoplastic composition to ambient temperature is usually achieved by blowing ambient or sub-ambient temperature air over the extruded thermoplastic composition. It can be referred to as quenching or super-cooling because the change in temperature is usually greater than 100° C. and most often greater than 150° C. over a relatively short time frame, such as in seconds.

Multicomponent fibers can be cut into relatively short lengths, such as staple fibers which generally have lengths in the range of about 25 to about 50 millimeters and short-cut fibers which are even shorter and generally have lengths less than about 18 millimeters. See, for example, U.S. Pat. No. 4,789,592 to Taniguchi et al, and U.S. Pat. No. 5,336,552 to Strack et al., both of which are incorporated herein by reference in their entirety.

The resultant multicomponent fibers of the present invention are desired to exhibit an improvement in hydrophilicity, evidenced by a decrease in the contact angle of water in air. The contact angle of water in air of a fiber sample can be measured as either an advancing or a receding contact angle value because of the nature of the testing procedure. The advancing contact angle generally measures a material's initial response to a liquid, such as water. The receding contact angle generally gives a measure of how a material will perform over the duration of a first insult, or exposure to liquid, as well as over following insults. A lower receding contact angle means that the material is becoming more hydrophilic during the liquid exposure and will generally then be able to transport liquids more consistently. The receding contact angle data is used to establish the highly hydrophilic nature of a multicomponent fiber of the present invention although it is preferable that a decrease in the advancing contact angle of the multicomponent fiber also takes place.

Thus, in one embodiment of the present invention, it is desired that the thermoplastic composition or a multicomponent fiber exhibit a Receding Contact Angle value that is beneficially less than about 55 degrees, more beneficially less than about 40 degrees, suitably less than about 25 degrees, more suitably less than about 20 degrees, and most suitably less than about 10 degrees, wherein the receding contact angle is determined by the method that is described in the Test Methods section herein.

Typical aliphatic polyester-based materials often undergo heat shrinkage during downstream thermal processing. The heat-shrinkage mainly occurs due to the thermally-induced chain relaxation of the polymer segments in the amorphous phase and incomplete crystalline phase. To overcome this problem, it is generally desirable to maximize the crystallization of the material before the bonding stage so that the thermal energy goes directly to melting rather than to allow for chain relaxation and reordering of the incomplete crystalline structure. The typical solution to this problem is to subject the material to a heat-setting treatment. As such, when prepared materials, such as fibers, are subjected to heat-setting upon reaching a bonding roll, the fibers won't substantially shrink because such fibers are already fully or highly oriented. The present invention alleviates the need for this additional processing step because of the morphology of the multicomponent fiber of the present invention. As discussed earlier, the polyolefin microfibers generally provide a reinforcing structure which minimizes the expected heat shrinkage of the aliphatic polyester.

In one embodiment of the present invention, it is desired that the thermoplastic composition or a multicomponent fiber exhibit an amount of shrinking, as quantified by a Heat Shrinkage value, at a temperature of about 100° C., that is beneficially less than about 10 percent, more beneficially less than about 5 percent, suitably less than about 2 percent, and more suitably less than about 1 percent, wherein the amount of shrinking is based upon the difference between the initial and final lengths of a fiber divided by the initial length multiplied by 100. The method by which the amount of shrinking that a fiber exhibits may be determined is included in the Test Methods section herein.

The multicomponent fibers of the present invention are suited for use in disposable products including disposable absorbent products such as diapers, adult incontinent products, and bed pads; in catamenial devices such as sanitary napkins, and tampons; and other absorbent products such as wipes, bibs, wound dressings, and surgical capes or drapes. Accordingly, in another aspect, the present invention relates to a disposable absorbent product comprising the multicomponent fibers of the present invention.

In one embodiment of the present invention, the multicomponent fibers are formed into a fibrous matrix for incorporation into a disposable absorbent product. A fibrous matrix may take the form of, for example, a fibrous nonwoven web. Fibrous nonwoven webs may be made completely from the multicomponent fibers of the present invention or they may be blended with other fibers. The length of the fibers used may depend on the particular end use contemplated. Where the fibers are to be degraded in water as, for example, in a toilet, it is advantageous if the lengths are maintained at or below about 15 millimeters.

In one embodiment of the present invention, a disposable absorbent product is provided, which disposable absorbent product comprises a liquid-permeable topsheet, a backsheet attached to the liquid-permeable topsheet, and an absorbent structure positioned between the liquid-permeable topsheet and the backsheet, wherein the backsheet comprises multicomponent fibers of the present invention.

Exemplary disposable absorbent products are generally described in U.S. Pat. Nos. 4,710,187; 4,762,521; 4,770,656; and 4,798,603; which references are incorporated herein by reference.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Test Methods

Melting Temperature

The melting temperature of a material was determined using differential scanning calorimetry. A differential scanning calorimeter, under the designation Thermal Analyst 2910 Differential Scanning Calorimeter, which was outfitted with a liquid nitrogen cooling accessory and used in combination with Thermal Analyst 2200 analysis software (version 8.10) program, both available from T.A. Instruments Inc. of New Castle, Del., was used for the determination of melting temperatures.

The material samples tested were either in the form of fibers or resin pellets. It is preferred to not handle the material samples directly, but rather to use tweezers and other tools, so as not to introduce anything that would produce erroneous results. The material samples were cut, in the case of fibers, or placed, in the case of resin pellets, into an aluminum pan and weighed to an accuracy of 0.01 mg on an analytical balance. If needed, a lid was crimped over the material sample onto the pan.

The differential scanning calorimeter was calibrated using an indium metal standard and a baseline correction performed, as described in the manual for the differential scanning calorimeter. A material sample was placed into the test chamber of the differential scanning calorimeter for testing and an empty pan is used as a reference. All testing was run with a 55 cubic centimeter/minute nitrogen (industrial grade) purge on the test chamber. The heating and cooling program is a 2 cycle test that begins with equilibration of the chamber to −75° C., followed by a heating cycle of 20° C./minute to 220° C., followed by a cooling cycle at 20° C./minute to −75° C., and then another heating cycle of 20° C./minute to 220° C.

The results were evaluated using the analysis software program wherein the glass transition temperature (Tg) of inflection, endothermic and exothermic peaks were identified and quantified. The glass transition temperature was identified as the area on the line where a distinct change in slope occurs and then the melting temperature is determined using an automatic inflection calculation.

Apparent Viscosity

A capillary rheometer, under the designation Göttfert Rheograph 2003 capillary rheometer, which was used in combination with WinRHEO (version 2.31) analysis software, both available from Göttfert Company of Rock Hill, S.C., was used to evaluate the apparent viscosity rheological properties of material samples. The capillary rheometer setup included a 2000 bar pressure transducer and a 30 mm length/30 mm active length/1 mm diameters mm height/180° run in angle, round hole capillary die.

If the material sample being tested demonstrates or is known to have water sensitivity, the material sample is dried in a vacuum oven above its glass transition temperature, i.e. above 55 or 60° C. for poly(lactic acid) materials, under a vacuum of at least 15 inches of mercury with a nitrogen gas purge of at least 30 standard cubic feet per hour for at least 16 hours.

Once the instrument is warmed up and the pressure transducer is calibrated, the material sample is loaded incrementally into the column, packing resin into the column with a ramrod each time to ensure a consistent melt during testing. After material sample loading, a 2 minute melt time precedes each test to allow the material sample to completely melt at the test temperature. The capillary rheometer takes data points automatically and determines the apparent viscosity (in Pascal.second) at 7 apparent shear rates (in second$^{-1}$): 50, 100, 200, 500, 1000, 2000, and 5000. When examining the resultant curve it is important that the curve be relatively smooth. If there are significant deviations from a general curve from one point to another, possibly due to air in the column, the test run should be repeated to confirm the results.

The resultant rheology curve of apparent shear rate versus apparent viscosity gives an indication of how the material sample will run at that temperature in an extrusion process. The apparent viscosity values at a shear rate of at least 1000 second$^{-1}$ are of specific interest because these are the typical conditions found in commercial fiber spinning extruders.

Molecular Weight

A gas permeation chromatography (GPC) method is used to determine the molecular weight distribution of samples, such as of poly(lactic acid) whose weight average molecular weight ($M_w$) is between about 800 to about 400,000.

The GPC is set up with two PLgel Mixed K linear 5 micron, 7.5×300 millimeter analytical columns in series. The column and detector temperatures are 30° C. The mobile phase is high-performance liquid chromatography (HPLC) grade tetrahydrofuran (THF). The pump rate is 0.8 milliliter per minute with an injection volume of 25 microliters. Total run time is 30 minutes. It is important to note that new analytical columns must be installed about every 4 months, a new guard column about every month, and a new in-line filter about every month.

Standards of polystyrene polymers, obtained from Aldrich Chemical Co., should be mixed into a solvent of dichloromethane(DCM):THF (10:90), both HPLC grade, in order to obtain 1 mg/mL concentrations. Multiple polystyrene standards can be combined in one standard solution provided that their peaks do not overlap when chromatographed. A range of standards of about 687 to 400,000 molecular weight should be prepared. Examples of standard mixtures with Aldrich polystyrenes of varying weight average molecular weights include: Standard 1 (401,340; 32,660; 2,727), Standard 2 (45,730; 4,075), Standard 3 (95,800; 12,860) and Standard 4 (184,200; 24,150; 687).

Next, prepare the stock check standard. Dissolve 10 g of a 200,000 molecular weight poly(lactic acid) standard, Cata-log#19245 obtained from Polysciences Inc., to 100 ml of HPLC grade DCM to a glass jar with a lined lid using an orbital shaker (at least 30 minutes). Pour out the mixture onto a clean, dry, glass plate and first allow the solvent to evaporate, then place in a 35° C. preheated vacuum oven and dry for about 14 hours under a vacuum of 25 mm of mercury. Next, remove the poly(lactic acid) from the oven and cut the film into small strips. Immediately grind the samples using a grinding mill (with a 10 mesh screen) taking care not to add too much sample and causing the grinder to freeze up. Store a few grams of the ground sample in a dry glass jar in a dessicator, while the remainder of the sample can be stored in the freezer in a similar type jar.

It is important to prepare a new check standard prior to the beginning of each new sequence and, because the molecular weight is greatly affected by sample concentration, great care should be taken in its weighing and preparation. To prepare the check standard weigh out 0.0800 g±0.0025 g of 200,000 weight average molecular weight poly(lactic acid) reference standard into a clean dry scintillation vial. Then, using a volumetric pipet or dedicated repipet, add 2 ml of DCM to the vial and screw the cap on tightly. Allow the sample to dissolve completely. Swirl the sample on an orbital shaker, such as a Thermolyne Roto Mix (type 51300) or similar mixer, if necessary. To evaluate whether is it dissolved hold the vial up to the light at a 45° angle. Turn it slowly and watch the liquid as it flows down the glass. If the bottom of the vial does not appear smooth, the sample is not completely dissolved. It may take the sample several hours to dissolve. Once dissolved, add 18 ml of THF using a volumetric pipet or dedicated repipet, cap the vial tightly and mix.

Sample preparations begins by weighing 0.0800 g±0.0025 g of the sample into a clean, dry scintillation vial (great care should also be taken in its weighing and preparation). Add 2 ml of DCM to the vial with a volumetric pipet or dedicated repipet and screw the cap on tightly. Allow the sample to dissolve completely using the same technique described in the check standard preparation above. Then add 18 ml of THF using a volumetric pipet or dedicated repipet, cap the vial tightly and mix.

Begin the evaluation by making a test injection of a standard preparation to test the system equilibration. Once equilibration is confirmed inject the standard preparations. After those are run, first inject the check standard preparation and then the sample preparations. Inject the check standard preparation after every 7 sample injections and at the end of testing. Be sure not to take any more than two injections from any one vial, and those two injections must be made within 4.5 hours of each other.

There are 4 quality control parameters to assess the results. First, the correlation coefficient of the fourth order regression calculated for each standard should be not less than 0.950 and not more than 1.050. Second, the relative standard deviation of all the weight average molecular weights of the check standard preparations should not be more than 5.0 percent. Third, the average of the weight average molecular weights of the check standard preparation injections should be within 10 percent of the weight average molecular weight on the first check standard preparation injection. Lastly, record the lactide response for the 200 microgram per milliliter ($\mu$g/mL) standard injection on a SQC data chart. Using the chart's control lines, the response must be within the defined SQC parameters.

Calculate the Molecular statistics based on the calibration curve generated from the polystyrene standard preparations and constants for poly(lactic acid) and polystyrene in THF at 30° C. Those are: Polystyrene (K=14.1*10$^5$, alpha=0.700) and poly(lactic acid)(K=54.9*10$^5$, alpha=0.639).

Heat Shrinkage of Fibers

The required equipment for the determination of heat shrinkage include: a convection oven (Thelco model 160DM laboratory oven, available from Precision and Scientific Inc., of Chicago, Ill.), 0.5 g (+/−0.06 g) sinker weights, ½ inch binder clips, masking tape, graph paper with at least ¼ inch squares, foam posterboard (11 by 14 inches) or equivalent substrate to attach the graph paper and samples to. The convection oven should be capable of a temperature of about 100° C.

Fiber samples are melt spun at their respective spinning conditions. In general, a 30 filament bundle is preferred and mechanically drawn to obtain fibers with a jetstretch ratio of beneficially 224 or higher. Only fibers of the same jetstretch ratio can be compared to one another in regards to their heat shrinkage. The jetstretch ratio of a fiber is the ratio of the speed of the drawdown roll divided by the linear extrusion rate (distance/time) of the melted polymer exiting the spinneret. The spun fiber is usually collected onto a bobbin using a winder. The collected fiber bundle is separated into 30 filaments, if a 30 filament bundle has not already been obtained, and cut into 9 inch lengths.

The graph paper is taped onto the posterboard where one edge of the graph paper is matched with the edge of the posterboard. One end of the fiber bundle is taped, no more than the end 1 inch. The taped end is clipped to the posterboard at the edge where the graph paper is matched up such that the edge of the clip rests over one of the horizontal lines on the graph paper while holding the fiber bundle in place (the taped end should be barely visible as it is secured under the clip). The other end of the bundle is pulled taught and lined up parallel to the vertical lines on the graph paper. Next, at 7 inches down from the point where the clip is binding the fiber, pinch the 0.5 g sinker around the fiber bundle. Repeat the attachment process for each replicate. Usually, 3 replicates can be attached at one time. Marks can be made on the graph paper to indicate the initial positions of the sinkers. The samples are placed into the oven at a temperature of about 100° C. such that the samples hang vertically and do not touch the posterboard. At time intervals of 5, 10 and 15 minutes quickly mark the new location of the sinkers on the graph paper and return samples to the oven.

After the testing is complete, remove the posterboard and measure the distances between the origin (where the clip held the fibers) and the marks at 5, 10 and 15 minutes with a ruler graduated to 1/16 inch. Three replicates per sample is recommended. Calculate averages, standard deviations and percent shrinkage. The percent shrinkage is calculated as (initial length—measured length) divided by the initial length and multiplied by 100. As reported in the examples herein and as used throughout the claims, the Heat Shrinkage value represents the amount of heat shrinkage that a fiber sample exhibits at a temperature of about 100° C. for a time period of about 15 minutes, as determined according to the preceding test method.

Contact Angle

The equipment includes a DCA-322 Dynamic Contact Angle Analyzer and WinDCA (version 1.02) software, both available from ATI-CAHN Instruments, Inc., of Madison, Wis. Testing was done on the "A" loop with a balance stirrup attached. Calibrations should be done monthly on the motor and daily on the balance (100 mg mass used) as indicated in the manual.

Thermoplastic compositions are spun into fibers and the freefall sample (jetstretch of 0) is used for the determination of contact angle. Care should be taken throughout fiber preparation to minimize fiber exposure to handling to ensure that contamination is kept to a minimum. The fiber sample is attached to the wire hanger with scotch tape such that 2–3 cm of fiber extends beyond the end of the hanger. Then the fiber sample is cut with a razor so that 1.5 cm is extending beyond the end of the hanger. An optical microscope is used to determine the average diameter (3 to 4 measurements) along the fiber.

The sample on the wire hanger is suspended from the balance stirrup on loop "A". The immersion liquid is distilled water and it is changed for each specimen. The specimen parameters are entered (i.e. fiber diameter) and the test started. The stage advances at 151.75 microns/second until it detects the Zero Depth of Immersion when the fiber contacts the surface of the distilled water. From the Zero Depth of Immersion, the fiber advances into the water for 1 cm, dwells for 0 seconds and then immediately recedes 1 cm. The auto-analysis of the contact angle done by the software determines the advancing and receding contact angles of the fiber sample based on standard calculations identified in the manual. Contact angles of 0 or <0 indicate that the sample has become totally wettable. Five replicates for each sample are tested and a statistical analysis for mean, standard deviation, and coefficient of variation percent are calculated. As reported in the examples herein and as used throughout the claims, the Advancing Contact Angle value represents the advancing contact angle of distilled water on a fiber sample determined according to the preceding test method. Similarly, as reported in the examples herein and as used throughout the claims, the Receding Contact Angle value represents the receding contact angle of distilled water on a fiber sample determined according to the preceding test method.

EXAMPLES

Example 1

Fibers were prepared using varying amounts of a poly (lactic acid), a polypropylene, and a compatibilizer. The poly(lactic acid) polymer (PLA) was obtained from Chronopol Inc., Golden, Colo., and had an L:D ratio of 100 to 0, a melting temperature of about 175° C., a weight average molecular weight of about 181,000, a number average molecular weight of about 115,000, a polydispersity index of about 1.57, and a residual lactic acid monomer value of about 2.3 weight percent. The polypropylene polymer (PP) was obtained from Himont Incorporated under the designation PF305 polypropylene polymer, which had a specific gravity of between about 0.88 to about 0.92 and a melting temperature of about 160° C. The compatibilizer was obtained from Petrolite Corporation of Tulsa, Okla., under the designation UNITHOX®480 ethoxylated alcohol, which had a melting temperature of about 160° C. and a number average molecular weight of about 2250.

To prepare a specific thermoplastic composition, the various components were first dry mixed and then melt blended in a counter-rotating twin screw to provide vigorous mixing of the components. The melt mixing involves partial or complete melting of the components combined with the shearing effect of rotating mixing screws. Such conditions are conducive to optimal blending and even dispersion of the components of the thermoplastic composition. Twin screw extruders such as a Haake Rheocord 90, available from Haake GmbH of Karlsautte, Germany, or a Brabender twin screw mixer (cat no 05-96-000) available from Brabender Instruments of South Hackensack, N.J., or other comparable twin screw extruders, are well suited to this task. The melted composition is cooled following extrusion from the melt mixer on either a liquid cooled roll or surface and/or by forced air passed over the extrudate. The cooled composition is then subsequently pelletized for conversion to fibers.

Converting these resins into fiber and nonwoven was conducted on a in-house 0.75 inch diameter extruder with a 24:1 L:D (length:diameter) ratio screw and three heating zones which feed into a transfer pipe from the extruder to the spin pack, which constitutes the 4th heating zone and contains a 0.62 inch (about 1.6 cm) diameter Koch® SMX type static mixer unit, available from Koch Engineering Company Inc. of New York, N.Y., and then into the spinning head (5th heating zone) and through a spin plate which is simply a plate with numerous small holes through which the molten polymer will be extruded through. The spin plate used herein had 15 to 30 holes, where each hole has a diameter of about 500 micrometers. The temperature of each heating zone is indicated sequentially under the extrusion temperatures heading in Table 2. The fibers are air quenched using air at a temperature range of 13° C. to 22° C., and drawn down by a mechanical draw roll and passed on to either a winder unit for collection, or to a fiber drawing unit for spunbond formation and bonding, or through accessory equipment for heat setting or other treatment before collection.

The fibers were evaluated for contact angle and heat shrinkage. The composition of the various fibers and the results of the evaluations are shown in Table 1.

TABLE 1

| Sample | Composition of Fiber (Wt %) | | | Contact Angle | | Heat Shrinkage |
|---|---|---|---|---|---|---|
| # | PLA | PP | Compatibilizer | Advancing | Receding | |
| *1 | 100% | — | — | 85.3° | 40.7° | 34% |
| *2 | — | 100% | — | 128.1° | 93.9° | 0% |
| *3 | — | 95% | 5% | 120.6° | 79° | — |
| *4 | — | 95% | 5% | 124.0° | 58.5° | 0% |
| *5 | 95% | — | 5% | 89.2° | 10.0° | — |
| *6 | 70% | 30% | — | 92.3° | 56.5° | 0% |
| 7 | 55% | 37% | 8% | 111.7° | 51.4° | 0% |
| 8 | 64% | 27% | 9% | 117.4° | 40.1° | 0% |
| 9 | 48% | 39% | 13% | 106.3° | 0° | 0% |
| 10 | 52% | 35% | 13% | 97.6° | 16.8° | 0% |
| 11 | 61% | 26% | 13% | 88.6° | 5.8° | 0% |
| 12 | 70% | 17% | 13% | 86.7° | 0° | 0% |
| 13 | 51% | 34% | 15% | 92.8° | 3.3° | 0% |
| 14 | 76.5% | 8.5% | 15% | 86.1° | 0° | 0% |

*Not an example of the present invention.

Example 2

Fibers were prepared using varying amounts of a polybutylene succinate, a polypropylene, and a compatibilizer. The polybutylene succinate (PBS) was obtained from Showa Highpolymer Co., Ltd., Tokyo, Japan, under the designation Bionolle 1020 polybutylene succinate, and had a melting temperature of about 95° C., a weight average molecular weight of between about 40,000 to about 1,000,000, a number average molecular weight of between about 20,000 to about 300,000, and a polydispersity index of between about 2 to about 3.3. The polypropylene polymer (PP) was obtained from Himont Incorporated under the designation PF305 polypropylene polymer, which had a specific gravity of between about 0.88 to about 0.92 and a melting temperature of about 160° C. The compatibilizer was obtained from Petrolite Corporation of Tulsa, Okla., under the designation UNITHOX®480 ethoxylated alcohol, which had a melting temperature of about 160° C. and a number average molecular weight of about 2250.

Fibers were prepared using a method essentially similar to the method described in Example 1.

The fibers were evaluated for contact angle and heat shrinkage. The composition of the various fibers and the results of the evaluations are shown in Table 2.

TABLE 2

| Sample | Composition of Fiber (Wt %) | | | Contact Angle | | Heat Shrinkage |
|---|---|---|---|---|---|---|
| # | PBS | PP | Compatibilizer | Advancing | Receding | |
| *15 | 100% | — | — | 76° | 0° | 0% |
| 16 | 61% | 26% | 13% | 21.8° | 0° | 0% |
| 17 | 70% | 17% | 13% | 24.1° | 0° | 0% |

*Not an example of the present invention.

Example 3

Fibers were prepared using varying amounts of a poly (lactic acid), a polyethylene, and a compatibilizer. The poly(lactic acid) polymer (PLA) was obtained from Chronopol Inc., Golden, Colo., and had an L:D ratio of 100 to 0, a melting temperature of about 175° C., a weight average molecular weight of about 181,000, a number average molecular weight of about 115,000, a polydispersity index of about 1.57, and a residual lactic acid monomer value of about 2.3 weight percent. The polyethylene polymer (PE) was obtained from The Dow Chemical Company, Midland, Mich., under the designation ASPUN® PE6811A polyethylene polymer and had a melting temperature of about 130° C. The compatibilizer was obtained from Petrolite Corporation of Tulsa, Okla., under the designation UNITHOX®480 ethoxylated alcohol, which had a melting temperature of about 160° C. and a number average molecular weight of about 2250.

Fibers were prepared using a method essentially similar to the method described in Example 1.

The fibers were evaluated for contact angle and heat shrinkage. The composition of the various fibers and the results of the evaluations are shown in Table 3.

TABLE 3

| Sample | Composition of Fiber (Wt %) | | | Contact Angle | | Heat Shrinkage |
|---|---|---|---|---|---|---|
| # | PLA | PE | Compatibilizer | Advancing | Receding | |
| 18 | 52% | 35% | 13% | 78.3° | 0° | 2% |
| 19 | 78% | 9% | 13% | 66.3° | 0° | 9% |

*Not an example of the present invention.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A method of making a multicomponent fiber comprising extruding a mixture of:
   (a) an aliphatic polyester polymer in a weight amount that is between about 45 to about 90 weight percent;

(b) polyolefin microfibers in a weight amount that is between greater than 0 to about 45 weight percent phase; and (c) a compatibilizer, which exhibits a hydrophilic-lipophilic balance ratio that is between about 10 to about 40, in a weight amount that is between about 7 to about 25 weight percent, wherein all weight percents are based on the total weight amount of the aliphatic polyester polymer; the polyolefin microfibers, and the compatibilizer present in the multicomponent fiber.

2. The method of claim 1, wherein the aliphatic polyester polymer forms a substantially continuous phase.

3. The method of claim 1, wherein the polyolefin microfibers have a diameter that is less than about 50 micrometers and the polyolefin microfibers form a substantially discontinuous phase encased within the aliphatic polyester polymer.

4. The method of claim 1, wherein the aliphatic polyester polymer comprises poly(lactic acid), polybutylene succinate, polybutylene succinate-co-adipate, polyhydroxybutyrate-co-valerate, polycaprolactone, sulfonated polyethylene terephthalate, mixtures of such polymers, or copolymers of such polymers.

5. The method of claim 4, wherein the aliphatic polyester polymer is poly(lactic acid).

6. The method of claim 1, wherein the polyolefin comprises homopolymers or copolymers having repeating units of ethylene, propylene, butene, pentene, hexene, heptene, octene, 1,3-butadiene, or 2-methyl-1,3-butadiene.

7. The method of claim 1, wherein the polyolefin comprises polyethylene or polypropylene.

8. The method of claim 1, wherein the polyolefin microfibers have a diameter that is less than about 25 micrometers.

9. The method of claim 1, wherein the polyolefin microfibers are present in a weight amount that is between about 5 to about 40 weight percent.

10. The method of claim 1, wherein the compatibilizer is an ethoxylated alcohol.

11. The method of claim 1, wherein the multicomponent fiber exhibits a Receding Contact Angle value that is less than about 55 degrees.

12. The method of claim 1, wherein the multicomponent fiber exhibits a Heat Shrinkage value that is less than about 10 percent.

13. The method of claim 1, wherein the multicomponent fiber comprise spunbonded fibers, sheath-core fibers, side-by-side fibers, meltblown fibers, or staple-length fibers.

14. A method of making a nonwoven web comprising:

interengaging a plurality of fibers to one another, wherein at least a portion of the fibers comprise the multicomponent fiber made by the method of claim 1.

15. A method of making a disposable absorbent product comprising:

joining a liquid-permeable topsheet, a backsheet, and an absorbent structure positioned between the liquid-permeable topsheet and the backsheet;

wherein the backsheet comprises a multicomponent fiber comprising:

(a) an aliphatic polyester polymer in a weight amount that is between about 45 to about 90 weight percent;

(b) polyolefin microfibers in a weight amount that is between greater than 0 to about 45 weight percent phase; and (c) a compatibilizer, which exhibits a hydrophilic-lipophilic balance ratio that is between about 10 to about 40, in a weight amount that is between about 7 to about 25 weight percent, wherein all weight percents are based on the total weight amount of the aliphatic polyester polymer; the polyolefin microfibers, and the compatibilizer present in the multicomponent fiber.

16. The method of claim 15, wherein the aliphatic polyester polymer forms a substantially continuous phase.

17. The method of claim 15, wherein the polyolefin microfibers have a diameter that is less than about 50 micrometers and the polyolefin microfibers form a substantially discontinuous phase encased within the aliphatic polyester polymer.

18. The method of claim 15, wherein the aliphatic polyester polymer comprises poly(lactic acid), polybutylene succinate, polybutylene succinate-co-adipate, polyhydroxybutyrate-co-valerate, polycaprolactone, sulfonated polyethylene terephthalate, mixtures of such polymers, or copolymers of such polymers.

19. The method of claim 15, wherein the aliphatic polyester polymer is poly(lactic acid).

20. A method of making a disposable absorbent product comprising:

joining the nonwoven web made by the method of claim 15 to one or more additional layers.

* * * * *

UNITED STATES PATENT AND TRADEMARK OFFICE
CERTIFICATE OF CORRECTION

PATENT NO. : 6,197,237 B1
DATED : March 6, 2001
INVENTOR(S) : Fu-Jya Daniel Tsai and Brian Thomas Etzel It is certified that error appears in the above-identified patent and that said Letters Patent is hereby corrected as shown below:

Title page,
Item [73], delete "Kimberly-Clark Corporation" and substitute -- Kimberly-Clark Worldwide, Inc. --.

Column 10,
Line 29, delete "spinbonded" and substitute -- spunbond --.
Line 31, delete "spinbonded" and substitute -- spunbond --.

Column 13,
Line 9, delete "diameters mm" and substitute -- diameter/0 mm --.

Column 20,
Line 45, delete "15" and substitute -- 14 --.

Signed and Sealed this

Fourth Day of February, 2003

JAMES E. ROGAN
*Director of the United States Patent and Trademark Office*